United States Patent [19]
Bonsignore et al.

[11] Patent Number: 5,563,238
[45] Date of Patent: Oct. 8, 1996

[54] WATER AND UV DEGRADABLE LACTIC ACID POLYMERS

[75] Inventors: Patrick V. Bonsignore, Joliet; Robert D. Coleman, Wheaton, both of Ill.

[73] Assignee: ARCH Development Corporation, Chicago, Ill.

[21] Appl. No.: 328,803

[22] Filed: Oct. 25, 1994

Related U.S. Application Data

[62] Division of Ser. No. 102,203, Aug. 5, 1993, Pat. No. 5,360,892.

[51] Int. Cl.$^6$ .............................. C08G 63/08; A61K 9/14
[52] U.S. Cl. .................. 528/354; 424/489; 424/490; 424/497; 428/480; 428/482; 525/415; 528/355; 528/361
[58] Field of Search ..................................... 424/489, 490, 424/497; 428/480, 482; 525/415; 528/354, 355, 361

[56] References Cited

U.S. PATENT DOCUMENTS

| | | | |
|---|---|---|---|
| 4,033,938 | 7/1977 | Augurt et al. | 528/354 |
| 4,526,938 | 7/1985 | Churchill et al. | 525/415 |
| 4,745,160 | 5/1988 | Churchill et al. | 525/415 |
| 4,861,627 | 8/1989 | Mathiowitz et al. | 424/462 |
| 5,360,892 | 11/1994 | Bonsignore et al. | 528/354 |

OTHER PUBLICATIONS

"Bioabsorbable Fibers of p–Dioxanone Copolymers", Bezwada et al., ACS Symposium Series, *Agricultural and Synthetic Polymers*, pp. 167–173, 1990.

"Polyesters Derived from 1,4–Oxathian–2–Ones", Huffman et al., *J. Polymer Science: Polymer Chemistry Edition*, vol. 23, pp. 843–849, 1985.

"The Role of Hydroperoxides in the Photooxidation of Crosslinked Polymer Coatings", Mielewski, et al., pp. 144–145, Sep. 1989.

"Rapidly Degraded Terpolymers of Dl–Lactide Glycolide, and α–Caprolactone with Increased Hydrophilicity by Copolymerization with Polyethers", Sawhney et al., *J. Biomedical Materials Research*, vol. 24, pp. 1397–1411, 1990.

"On the Kinetics of Polymer Degradation in Solution; Part XI–Radiolysis of Poly(Olefin Sulfones)", Horie et al., *Polymer Degradation and Stability*, 8(1984) 145–159.

*Primary Examiner*—Shelley A. Dodson
*Attorney, Agent, or Firm*—Reinhart, Boerner, Van Deuren, Norris & Rieselbach, s.c.

[57] ABSTRACT

A water and UV light degradable copolymer of monomers of lactic acid and a modifying monomer selected from the class consisting of ethylene glycol, propylene glycol, P-dioxanone, 1,5 dioxepan-2-one, 1,4-oxathialan-2-one, 1,4-dioxide and mixtures thereof. These copolymers are useful for waste disposal and agricultural purposes. Also disclosed is a water degradable blend of polylactic acid or modified polylactic acid and high molecular weight polyethylene oxide wherein the high molecular weight polyethylene oxide is present in the range of from about 2 by weight to about 50% by weight, suitable for films. A method of applying an active material selected from the class of seeds, seedlings, pesticides, herbicides, fertilizers and mixtures thereof to an agricultural site is also disclosed.

15 Claims, No Drawings

WATER AND UV DEGRADABLE LACTIC ACID POLYMERS

CONTRACTUAL ORIGIN OF THE INVENTION

The United States Government has rights in this invention pursuant to Contract No. W-31-109-ENG-38 between the U.S. Department of Energy and The University of Chicago, representing Argonne National Laboratory.

This is a divisional of application Ser. No. 08/102,703 filed on Aug. 5, 1993 now U.S. Pat. No. 5,360,892.

BACKGROUND OF THE INVENTION

The invention relates to modified polymers and polymer blends useful for waste disposal or for agricultural purposes to provide water or UV degradable materials which are environmentally safe. The materials are designed to degrade upon exposure to water or to UV light to environmentally safe naturally occurring materials. The modified polymers and polymer blends when used are also usable for garbage bags or other waste disposal purposes can be incinerated since upon burning only environmentally safe materials are produced.

It is now recognized that many plastic materials useful for packaging as well as waste disposal present serious environmental problems because they either do not degrade in landfills or produce toxic components upon incineration. More and more attention has been devoted to environmentally safe plastic materials, particularly since Congressional hearings have determined that over 135 thousand metric tons per year of plastic is discarded at sea alone with some 639,000 plastic containers and bags tossed into the ocean every day. In addition to this intolerable situation, the amount of plastic materials used for packaging as well as garbage disposal which do not degrade has caused landfill areas previously thought to be entirely adequate for urban disposal sites to become filled and unusable. Waste disposal has become a very serious problem in this country as well as world-wide.

Accordingly, there is a need to provide plastic materials suitable for packaging and waste disposal which at the same time will also be biodegradable to products which are environmentally safe.

Recently, it has been determined that high carbohydrate waste presently produced in the United States as cheese whey and in conjunction with potato processing facilities is convertible in an environmentally benign process to provide a feed stream for lactic acid. Lactic acid is desirable because it is a naturally occurring compound which degrades to environmentally safe products. In addition, it has been discovered that oligomers of polylactic acid are not only environmentally safe but preferable and are useful as plant growth promoters, see U.S. Pat. No. 4,813,997 to Kinnersley et al., issued Mar. 21, 1989. With the discovery by Kinnersley et al. and the conversion of high carbohydrate food waste to feed stocks for lactic acid, a result of research at Argonne National Laboratory, it has become feasible through the present invention to formulate various copolymers and blends of polylactic acid for a wide range of agricultural and packaging uses which meet all the objectives set forth above and provide environmentally safe materials to replace presently used plastics that are difficult to dispose of in a safe manner.

Accordingly, it is an object of the invention to provide water and/or UV light degradable modified polylactic acid polymers or blends thereof useful for the agricultural and/or packaging and/or waste disposal industries.

Another object of the invention is to provide water degradable or UV light degradable polylactic acid polymers and copolymers which may be used as agricultural coatings and mulches which degrade in the field to provide environmentally safe materials as well as plant growth promoters.

Another object of the invention is to provide a water degradable modified polylactic acid polymer comprising a copolymer of monomers of lactic acid and a modifying monomers selected from the class consisting of ethylene glycol, propylene glycol, p-dioxanone, 1,5 dioxepan-2-one, 1,4 -oxathialan-2-one, 4,4-dioxide and mixtures thereof, wherein the ethylene glycol is present in the range of from about 5% by weight to about 40% by weight, wherein the propylene glycol is present in the range of from about 5% by weight to about 40% by weight, wherein the p-dioxanone, 1,5 dioxepan-2-one or the 1,4-oxathialan-2-one, 4,4-dioxide is present in the range of from about 2% by weight to about 40% by weight, the modifying polymer not exceeding about 40% by weight of the modified polylactic acid copolymer.

A still further object of the invention is to provide a water and UV degradable polylactic acid polymer comprising a copolymer of polylactic acid and a modifying monomer selected from the class consisting of p-dioxanone present in an amount up to about 20% by weight, 1,5 dioxepan-2-one present in an amount up to about 20% by weight, and 1,4 oxathialan-2-one, 4,4 dioxide present in an amount up to about 20% by weight, or mixtures thereof, the modifying monomer being present in an amount not greater than about 20% by weight.

Still another object of the invention is to provide a water degradable polylactic acid polymer comprising an alloy of polylactic acid and high molecular weight polyethylene oxide wherein the high molecular weight polyethylene oxide is present in the range of from about 2 to about 50% by weight.

A final object of the invention is to provide a method of applying an active material selected from the class of seeds, seedlings, pesticides, herbicides, fertilizers and mixtures thereof of an to agricultural site comprising providing a copolymer of monomers of lactic acid and a modifying monomer selected from the class consisting of ethylene glycol, polypropylene glycol, p-dioxanone, 1,5 dioxepan-2-one, 1,4-oxathialan-2-one, 4,4-dioxide and mixtures thereof, wherein the ethylene glycol is present in the range of from about 5% by weight to about 40% by weight, wherein the propylene glycol is present in the range of from about 5% by weight to about 40% by weight, wherein the p-dioxanone, 1,5 dioxepan-2-one or the 1,4-oxathialan-2-one, 4, 4-dioxide is present in the range of from about 2% by weight to about 40% by weight, the modifying polymer not exceeding about 40% by weight of the modified polylactic acid polymer, forming a combination of the copolymer and the active ingredients wherein the active ingredients are present in the range of from about 60% to about 98% by weight of the combination, and applying the combination to the agricultural site.

The invention consists of certain novel features and a combination of parts hereinafter fully described, and particularly pointed out in the appended claims, it being understood that various changes in the details may be made without departing from the spirit, or sacrificing any of the advantages of the present invention.

DETAILED DESCRIPTION OF THE INVENTION

Polymers and copolymers of lactic acid are transparent, colorless thermoplastics with a wide range of physical properties that mimic those of many conventional thermoplastics. When exposed to moisture or biological and certain of the copolymers thereof show no degradation of the molecular weight. But after six months, physical properties drop significantly. For instance, water degradable modified polylactic acid copolymers may be made from monomers of lactic acid and modifying monomers selected from the class consisting of ethylene glycol, propylene glycol, p-dioxanone, 1,5 dioxepan-2-one, 1,4-oxathialan-2-one, 4,4-dioxide and various mixtures thereof. The physical properties such as crystallinity, melting point, degradation rate, elasticity and the like can be varied depending upon the amount and the type of copolymer formed.

By way of example, without limiting the scope of the invention, for copolymers of lactic and glycolic acids, the crystallinity varies from small for 100% lactic acid to high for essentially all glycolic acid. Similarly, the melting point will vary from a low melting point of about 53° C. for 100% lactic acid to a high melting point of close to 230° C. for principally all glycolic acid. The elasticity of the material will vary from glassy materials which are relatively non-elastic to high-modulus elastic materials, and the degradation rates will vary from intermediate to fast to very slow to none depending upon the amounts of polylactic acid or polyglycolic acid utilized.

In general, the various physical attributes discussed above can be varied among a wide range of physical properties depending upon the types and amounts of copolymers used for the final material, it being important that depending upon the end usage desired that the modifying polymer for the polylactic acid be present in the range from about 5% by weight to about 40% by weight so as to provide a water degradable modified polylactic acid copolymer which has suitable physical properties for the end use selected.

It is contemplated that the various copolymers of polylactic acid may be useful for a variety of agricultural and waste management uses. For instance, the copolymers may be used as coatings on or as matrices for seeds, seedlings, pesticides, herbicides, fertilizers and mixtures thereof, wherein the coating or matrices provide a controlled release of the coated or embedded material depending upon the thickness of the coating or percent of active ingredient embedded in the matrix. The coatings may have a thickness in the range of from about 0.25 microns to about 4 microns, so that release rates can be varied as required. The active ingredients, such as seeds, pesticides, herbicides, fertilizers or mixtures thereof also may be mixed with the copolymer and extruded as pellets, with the active ingredient dispersed in a matrix of the copolymer. Here, the release of active ingredients will be controlled by varying the type of copolymer and the amount thereof present. It is preferred that where the copolymer is used as a matrix for an active ingredient, it is present in the range of from about 2% to about 40% by weight, that is, the active ingredient is present in the range of from about 60% to about 98%. Accordingly, it is seen that fertilizers, for instance such as urea or other nitrogen rich fertilizers can be coated with various thicknesses of coating or dispersed in a matrix to provide a continuing release of the coated or dispersed materials over a wide range of time so as to prevent crop burning and other undesirable side effects when too much urea or other fertilizer is released at any one time.

In general, the copolymers of lactic acid are useful with molecular weights in a range of from about 20,000 to about 100,000 for the uses aforesaid as coatings or matrices. Where sheet materials are desired, such as in agricultural mulches and the like, molecular weights of greater than about 25,000 are preferred and in particular, molecular weights in the range from 25,000 to 100,000 are preferred for agricultural mulches which upon time and exposure to moisture and UV light will degrade to the constituent lactic acid and other monomers.

The copolymer, particularly for agricultural use will often be present as a matrix or as a coating for the active material. Previously, polylactic acid has been used as an encapsulator in the medical field and preparation of encapsulated active materials with polylactic acid coatings has been taught by Ogawa et al. in a paper entitled *New Technique to Efficiently Entrap LeuProlide Acetate into Microcapsules of Polylactic Acid or CoPoly (Lactic/Glycolic) Acid* in Chem. Pharm. Bull. 36(3) 1095–1103 (1988), the disclosure of which is incorporated herein by reference. Further, a process of preparing microcapsules of lactides or lactide copolymers has been patented by Gardner, Jan. 20, 1987, U.S. Pat. No. 4,637,905, the disclosure of which is incorporated herein by reference. Similarly, and also in the pharmaceutical field, micro encapsulation has been taught by Lapka et al. U.S. Pat. No. 4,622,244, issued Nov. 11, 1986, the disclosure of which is incorporated herein by reference.

The various modifying monomers which form the new copolymers herein before disclosed, provide a wide range of physical properties from highly crystalline to amorphous materials and from high to low melting point materials, thereby providing controlled degradation rates upon exposure to either UV light or to moisture or to both.

While Sinclair in an article entitled *Slow-Release Pesticide System, Polymers of Lactic and Glycolic Acids as Ecogolically Beneficial, Cost-Effective Encapsulating Materials*, teaches the use of combinations of glycolic and lactic acids as a matrixes for a pesticide, Sinclair does not show or suggest the use of the modified copolymers of lactic acid of this invention. Specifically, the polypropylene glycol and polyethylene glycol used as modifiers are a different class of materials than the glycolic acid taught by Sinclair.

The present invention permits a copolymer to be designed to control the release rate of the active material to the environment. Where the active material is a high urea content fertilizer, the controlled degradation of the matrix permits the urea to be released at a rate which prevents crop burning and other undesirable side effects. Where the active material is a herbicide or pesticide, the controlled degradation of the matrix permits continual application of the pesticide or herbicide over a prolonged period of time, thereby permitting fewer applications by the farmer and ultimately, releasing less of the active material into the environment since only so much as needed is added at any one time.

It can be seen therefore that increased savings are available to the farmer, both due to fewer applications as well as to administering less of the active material overall. Another added feature and benefit of the present invention is the use of modified polylactic polymers as matrixes or coatings for seeds or seedlings which when germinating or growing are provided with a concentration of growth promoting oligomers of polylactic acid or the disclosed copolymers as the modified polylactic acid copolymer degrades in situ. Whenever the disclosed copolymers degrade in an agricultural site, there will be a variety of oligomers of polylactic acid and copolymers thereof present in a wide variety of chain length or molecular weights. Some of these materials are proven growth promoters.

Both agricultural and waste disposal uses require plastic materials for a wide variety of products including inter alia, agricultural mulches and garbage bags, which depending on the polymers selected, degrade over a wide range of time. For instance, an agricultural mulch may be designed to degrade from a few days to a few months. While a plastic garbage bag certainly will not be designed to degrade over a few days. For films, a preferred blend is polylactic acid and high molecular weight polyethylene oxide. It has been found that a high molecular weight polyethylene oxide of greater than about 100,000 molecular weight blended with a polylactic acid having a molecular weight in the range of from about 25,000 to approximately 100,000 provides a superior film. Particularly, it has been found that when the high molecular weight polyethylene oxide is present as a blend or alloy in the range of from about 2% by weight to about 50% by weight of the total polymer material, a superior film occurs. It should be understood that this is not a copolymer as previously discussed, but rather is a physical blend or alloy of polylactic acid and a high molecular weight polyethylene oxide wherein a copolymer is not formed. However, these particular blends of polylactic acid, modified as previously taught or with the addition of a glycolic acid monomer or unmodified and high molecular weight polyethylene oxide provide films having superior physical properties.

Further, when used as a film for trash bags and the like, the film can be designed so as to degrade without the presence of UV light such as in conditions which occur in landfills.

While there has been disclosed what is considered to be the preferred embodiment of the present invention, it is understood that various changes in the details may be made without departing from the spirit, or sacrificing any of the advantages of the present invention.

The embodiments of the invention in which an exclusive property or privilege is claimed are defined as follows:

1. A method of promoting plant development, comprising:
   providing an active material, said material having incorporated therewith a polymer consisting essentially of monomers selected from the group consisting of lactic acid, glycolic acid, and mixtures thereof, and at least one of p-dioxanone, 1,5-dioxepan-2-one, 1,4-oxathia-2-one-4, 4-dioxide, ethylene glycol, and propylene glycol;
   introducing said material to a growth medium, whereby under environmental conditions oligomers from the group consisting of lactic acid, glycolic acid, and mixtures thereof are available for plant growth and development.

2. The method as defined in claim 1 wherein said active material is selected from the group consisting of seeds, seedlings, pesticides, herbicides, fertilizers, and mixtures thereof.

3. The method as defined in claim 2 wherein said polymer is a coating about said active material.

4. The method as defined in claim 3 wherein said coating has a thickness of about 0.25–4.0 microns.

5. The method as defined in claim 3 wherein said coating is about 2–40 weight percent.

6. A method for preparing plant growth promoting oligomers comprising:
   providing a polymeric material of monomers selected from the group consisting of lactic acid, glycolic acid, and mixtures thereof, and at least one of p-dioxanone, 1,5-dioxepan-2-one, 1,4-oxathia-2-one-4, 4-dioxide, ethylene glycol, and propylene glycol; and
   applying said polymeric material to an agricultural site for degradation to said oligomers of lactic acid, glycolic acid and mixtures thereof.

7. The method as defined in claim 6 wherein said polymeric material is polylactic acid.

8. The method as defined in claim 7 wherein said polymeric material is a film sheet.

9. The method as defined in claim 7 wherein said polylactic acid is physically blended with polyethylene oxide, said oxide present at about 2–50 weight percent of the total polymeric material.

10. A method for controlling the rate of release of an active material to an agricultural site, comprising:
    providing a plant-active material;
    combining said active material with a polymer consisting essentially of monomers selected from the group consisting of lactic acid, glycolic acid, and mixtures thereof, and at least one of p-dioxanone, 1,5-dioxepan-2-one, 1,4-oxathia-2-one-4, 4-dioxide, ethylene glycol, and propylene glycol; and
    applying said polymer/material combination to an agricultural site, whereby degradation of said polymer extends application of said active material.

11. The method as defined in claim 10 wherein said active material is selected from the group consisting of seeds, seedlings, pesticides, herbicides, fertilizers, and mixtures thereof.

12. The method as defined in claim 11 wherein said polymer is a coating about said active material.

13. The method as defined in claim 12 wherein said coating has a thickness of about 0.25–4.0 microns.

14. The method as defined in claim 12 wherein said coating is about 2–40 weight percent.

15. The method as defined in claim 10 wherein said application further provides growth promoting oligomers of said polymer.

* * * * *